United States Patent [19]
Geselowitz et al.

[11] Patent Number: 5,376,525
[45] Date of Patent: Dec. 27, 1994

[54] METHOD FOR DETECTION OF MYCOPLASMA

[75] Inventors: Daniel A. Geselowitz; Leonard M. Neckers, both of Bethesda; Lyn D. Olson, Silver Spring, all of Md.

[73] Assignee: The United States of America as represented by the Department of Health and Human Services, Washington, D.C.

[21] Appl. No.: 950,020

[22] Filed: Sep. 24, 1992

[51] Int. Cl.$^5$ .................. C12Q 1/68; C12P 19/34; G01N 33/50

[52] U.S. Cl. .................. 435/6; 435/91.1; 435/91.32; 436/63; 935/77; 935/78

[58] Field of Search .............. 435/6, 91, 91.1, 91.32; 935/77, 78; 436/63, 94

[56] References Cited

PUBLICATIONS

Neale (J. Bacteriol (1984) 158: 943-947.
Gebeyehu Nucl Acids Res 1987 15: 4513-4534.
Lau et al Carcinogenesis (1991) 12: 885-893.
Vlasov et al, Bropolim Kletka 1991 7(5) 37.
Van Kuppeveld et al Applied and Environmental Microbiology (1992) 58: 2606-2615.
Sasaki, et al, Microbiol Immunol (1992) 36: 21-28.
Hellung-Larsen, et al., "Influence of Mycoplasma Infection on the Incorporation of Different Precursors into RNA Components of Tissue Culture Cells", Experimental Cell Research 99, pp. 295-300, 1976.
Merkenschlager, et al., "Rate of Incorporation of Radiolabelled Nucleosides does not Necessarily Reflect the Metabolic State of Cells in Culture: Effects of Latent Mycoplasma Contamination", Immunology 63, pp. 125-131, Aug. 27, 1988.
Schneider, et al., "Incorporation of Tritiated Uridine and Tritiated Uracil into RNA, A Simple Technique for the Detection of Mycoplasma Contamination of Cultured Cells", Experimental Cell Research 84, pp. 311-318, 1974.
McIvor, "Differences in Incorporation of Nucleic Acid Bases and Nucleosides by Various Mycoplasma and Acholeplasma Species", Journal of Bacteriology, vol. 133, No. 2, pp. 438-489, Feb. 13, 1978.
Harley, "HeLa Cell Nucleic Acid Metabolism, The Effect of Mycoplasma Contamination", Biochimica et Biophysica ACTA 213, pp. 171-182, Mar. 9, 1970.
Razin, S., "Nucleic Acid Precursor Requirements of Mycoplasma Laidlawii", Journal of General Microbiology, 28, pp. 243-250, 1962.
Hewish, "Incorporation of $^{32}$P into Ribosomal RNA, Transfer RNA and Inositol Hexaphosphate in Germinating Pea Cotyledons", Biochimica et Biophysica Acta, 228, pp. 509-516, 1971.
Trebichavsky, "Incorporation of Radiophosphorus into Nucleic Acids of Frog Embryo", Folia Biologica, pp. 54-58, 1970.
Razin, et al., "Rapid Detection of Mycoplasmal Infection: DNA Probes for Detection and Identification of Mycoplasmas", Israel Journal of Medical Sciences, vol. 23, pp. 735-741, 1987.
Gobel, et al., "Synthetic Oligonucleotide Probes Complementary to rRNA for Group and Species Specific Detection of Mycoplasmas", Israel Journal of Medical Sciences, vol. 23, pp. 742-746, 1987.
Gobel, et al., "Oligonucleotide Probes Complementary to Variable Regions of Ribosomal RNA Discriminate between Mycoplasma Species", Journal of General Microbiology, 133, pp. 1969-1974, 1987.
Mattsson, et al., "Detection of Mycoplasma Bovis and Mycoplasma Agalactiae by Oligonucleotide Probes (List continued on next page.)

Primary Examiner—Margaret Parr
Assistant Examiner—Carla Myers
Attorney, Agent, or Firm—Knobbe, Martens, Olson & Bear

[57] ABSTRACT

A method for detecting mycoplasma infection in a sample by contacting the sample with labeled oligonucleotides, then measuring incorporation (if any) of the label into mycoplasma RNA.

13 Claims, 2 Drawing Sheets

PUBLICATIONS

Complementary to 16s rRNA", Molecular and Cellular Probes, 5, pp. 27–35, 1991.

Plamer, et al., "Development and Evaluation of the Polymerase Chain Reaction to Detect Mycoplasma Genitalium", FEMS Microbiology Letters, 77, pp. 199–203, 1991.

Jensen, et al., "Polymerase Chain Reaction for Detection of Mycoplasma Genitalium in Clinical Samples", Journal of Clinical Microbiology, vol. 29, No. 1, pp. 46–50, Jan. 1991.

Harasawa, et al., "Detection of Mycoplasma Hypopneumoniae DNA by the Polymerase Chain Reaction", Molecular and Cellular Probes, 5, pp. 103–109, 1991.

Blanchard, et al., "Detection and Identification of Mycoplasmas by Amplification of rDNA", FEMS Microbiology Letters, 81, pp. 37–42, 1991.

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
        ( B ) CLONE: CLONE 1

( x i ) SEQUENCE DESCRIPTION: SEQ ID NO:1:

GATCATGCCC GGCAT         15

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA -continued ( i i i ) HYPOTHETICAL: NO ( i v ) ANTI-SENSE: NO ( v i i ) IMMEDIATE SOURCE:
        ( B ) CLONE: CLONE 2

( i x ) FEATURE:
        ( A ) NAME/KEY: modifiedbase
        ( B ) LOCATION: 15

( x i ) SEQUENCE DESCRIPTION: SEQ ID NO:2:

GATCATGCCC GGCAT         15

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
        ( B ) CLONE: CLONE 3

( x i ) SEQUENCE DESCRIPTION: SEQ ID NO:3:

GATCATGCCC GGCATA         16

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
        ( B ) CLONE: CLONE 4

( x i ) SEQUENCE DESCRIPTION: SEQ ID NO:4:

GCTGATCATG CCCGGCAT         18

( 2 ) INFORMATION FOR SEQ ID NO:5:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
        ( B ) CLONE: CLONE 5

( x i ) SEQUENCE DESCRIPTION: SEQ ID NO:5:

GATCATGCCC GGCATG         16

METHOD FOR DETECTION OF MYCOPLASMA

BACKGROUND

In 1693, contagious bovine pleuropneumonia, a fetal disease of cattle, was discovered in Germany, later reaching the United States in 1843. Louis Pasteur suggested that the cause was a specific ultramicroscopic agent, since bacteria could not be detected in serous exudate capable of producing the disease in cattle. Colonies produced by these agents were difficult to detect due to their small size and inability to absorb most stains. The organisms were simply too small to be defined morphologically at that time.

A number of similar microorganisms were later isolated from animals (including humans) and sewage between 1920 and 1940. These organisms were termed pleuropneumonia-like organisms (PPLO), and are now known as mycoplasmas. As obligate cellular parasites, mycoplasmas lack the rigid peptidoglycan cell wall of eubacteria, yet contain the machinery necessary for replication in a cell-free environment.

Over 100 mycoplasma species have been identified, including more than 11 species capable of affecting humans; some being the etiologic agents of disease. Mycoplasma species include animal, plant, and insect pathogens, in addition to a significant part of the normal microbial flora of most animals. One species, *Mycoplasma pneumoniae* is the etiologic agent responsible for primary atypical pneumonia. Several species of mycoplasmas also appear to be involved in some cases of non-gonococcal urethritis and pelvic inflammatory disease.

Mycoplasmas have the ability to pass through 450-nm filters, as do chlamydiae, rickettsiae, and viruses. However, mycoplasma differ from these other small infectious agents in being able to grow, albeit slowly, on artificial media. Many mycoplasmas are initially mistaken for viruses. Their filterability is due not only to their small size but also the inherent flexibility of their cell envelope. Since mycoplasmas are only surrounded by a lipid membrane, they have been designated as the class Mollicutes (L. mollis and cutis, soft skin).

Variations in the size and shape of mycoplasmas can be ascribed in part to the lack of a cell wall, as can the variable staining obtained with Gram stains. Electron microscopy has shown that mycoplasmas have a variable and pleomorphic cellular morphology, even within a pure culture.

Some organisms assume a predominantly spherical appearance (300–800 nm in diameter) while others may form filaments of uniform diameter (100–300 nm), varying in length from 3 $\mu$m to over 150 $\mu$m. Thin sections reveal a simple ultrastructure consisting of a cell membrane and cytoplasm, including ribosomes and the characteristic nucleoid. There are no intracellular membranous structures.

Most mycoplasmas will form very small colonies (50 $\mu$m–600 $\mu$m in diameter), which can normally only be seen with a low power microscope. The classic "fried egg" appearance of typical mycoplasma colonies is due to an opaque, granular central zone of growth down into the agar and a translucent peripheral growth zone on the surface. However, not all mycoplasmas produce colonies with a "fried egg" morphology, especially primary isolates. Variations in colonial morphology are frequently dependent on the constituents and hydration of the growth medium.

Mycoplasmas usually divide, like other prokaryotes, by binary fission. In some instances genomic replication and cytoplasmic division are not precisely synchronized and become dissociated. A lag in cytoplasmic division yields multinucleated filaments, which subsequently form chains of coccoid cells and then fragment into individual cells.

Mycoplasmas have a circular genome of double-stranded DNA, one-fifth to one-half as large as that in most bacteria. This is evidently the smallest genome that can code for all the products needed for self-reproduction in an artificial medium.

Mycoplasmas have exacting nutritional requirements, especially for the lipids essential to synthesize their plasma membrane. The nutritional requirement of many mycoplasmas for exogenous sterol is unique among prokaryotes. It is usually met by animal serum, which contains cholesterol bound to a lipoprotein.

Mycoplasmas are difficult to identify and in the past were consistently confused with L-forms of eubacteria. The difficulty in detecting mycoplasma has implications both in microbiology (e.g., contaminated cell cultures) and in human and veterinary medicine (e.g., mycoplasma infection).

Although these obligate cellular parasites have exacting requirements for growth, mycoplasma contamination of cell cultures remains a great problem for many researchers.

These frequently undetected parasites are common infectants of cell cultures (Barile (1979) *The Mycoplasmas*, J. G. Tully and S. Razin, eds.: 425–474; McGarrity, et al. (1985) *The Mycoplasmas*, M. F. Barile and S. Razin, eds.: 353–390; Stanbridge (1971) *Bacteriol* 35: 206–227). The precise effect of the contaminant on cell structure can vary with the species or strain of mycoplasma, in addition to the cell type and growth medium. The unpredictable effects of mycoplasma contamination of cell cultures have included virtually every cell parameter, including changes in cytokine production, increased or decreased viral production and chromosome breakage.

Despite the documented nuclease activity of mycoplasmas (Neimark (1964) *Nature* 203: 549–550; Razin, et al. (1964) *J. Gen. Microbiol.* 36: 323–332) and their nutritional requirement for nucleic acid precursors (Razin (1962) *J. Gen. Microbiol.* 28: 243–250; Razin, et al. (1960) *J. Gen. Microbiol.* 22: 504–519), there is little information relating to the influence of mycoplasma infection on molecular biology techniques such as antisense translation inhibition.

In the antisense oligonucleotide approach to gene therapy, specific oligonucleotides are introduced into target cells. Following internalization, the oligonucleotides interfere in a sequence-specific manner with the RNA translation mechanism. Despite numerous reports of antisense effects in mammalian cells resulting from exogenous addition of oligonucleotides, fundamental questions about the stability and uptake of these compounds remain (Neckers, et al. (1992) *CRC Crit. Rev. Oncogenesis* 3: 175–231). Even less is known about the pharmacokinetics of these reagents in vivo Plainly, factors affecting these parameters must be controlled.

Others have attempted to devise ways of easily and quickly detecting mycoplasma contamination in cell cultures without much success. In one experiment, over 90% of [$^3$H]Uracil was found to be incorporated into mycoplasma RNA in a contaminated cell culture while only 10% was incorporated into the growing culture cells. However, $^3$H is difficult to detect by autoradiography or a geiger counter, and therefore provided a very poor (and slow) method for identifying mycoplasma contamination. Extended periods of autoradiography are necessary to visualize the incorporation of [$^3$H]Uracil into RNA.

Tritium labeled thymidine ([$^3$H]T) and uridine ([$^3$H]U) have also been used in a bioassay based upon the degradation of ([$^3$H]T) by a cell free culture supernatant (Merkenschlager (1988) *Immunology* 63(1): 125-131). In this method, mycoplasma contamination was detected by pyrimidine phosphorylase activity on the labeled nucleotides.

Other experimenters have also used various tritium labeled nucleosides and found that mycoplasma RNA is tritiated by these compounds more efficiently than mammalian cells (Schneider (1974) *Experimental Cell Research* 84(1-2): 311-318; McIvor (1978) *Journal of Bacteriology* 135: 483-489). Although the uptake and incorporation of tritium-labeled nucleosides into mycoplasma RNA has been used to determine the extent of cell culture contamination, tritium's weak radioactivity has made rapid diagnosis difficult. Experiments involving stronger radioactive isotopes, such as $^{32}$P, were unsuccessful since the labeled nucleotides were inefficiently incorporated into the mycoplasma RNA (Hellung-Larsen (1976) *Experimental Cell Research* 99(2): 295-300).

An alternative method of detecting mycoplasma contamination in a cell culture involves using specific labeled probes that only hybridize with mycoplasma gene sequences (Gobel (1987) *Israel Journal of Medical Sciences* 23: 735-741). This procedure, however, also requires substantial preparation time to isolate the cell culture DNA, prepare the probe, and perform the hybridization assay.

It would be desirable to have a method which incorporated the ease of the metabolic techniques (e.g.: tritium experiments) with a stronger means of preferentially labeling the mycoplasma. Unfortunately, mycoplasma do not seem to take up the $^{32}$P labeled nucleotides at the fast rate seen with the tritium labeled nucleotides. The preferred embodiment of the present invention overcomes this problem by providing a method of quickly identifying mycoplasma contamination using high specific activity isotopes such as $^{32}$P and $^{35}$S.

SUMMARY OF THE INVENTION

Figure 1:
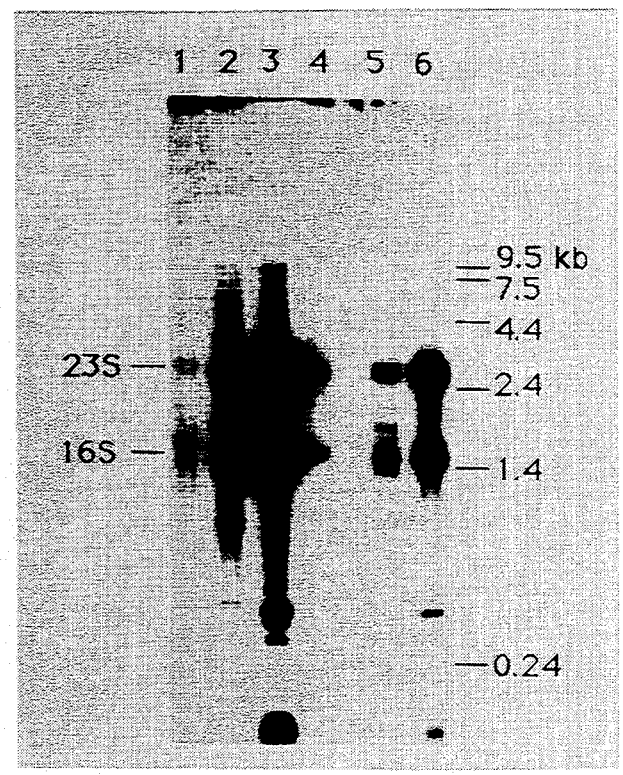
FIG. 1 Incorporation of radiophosphorus from 5'-end-labeled oligonucleotide 1 into RNA of four species of mycoplasma. Cultures were incubated for 2 h with approximately 10 μCi, and then the RNA was harvested and electrophoresed on a 1.2% agarose, formaldehyde, and MOPS gel and autoradiographed. Lane 1, *M. pneumoniae*; lane 2, *M. arginini*; lane 3, *M. fermentans*; lane 4, *M. hominis*; lane 5, *M. arginini*, lighter exposure; lane 6; *M. fermentans*, lighter exposure.

One preferred embodiment of the present invention relates to a method for detecting mycoplasma in a sample. In this embodiment, the steps comprise incubating the sample with oligonucleotides having a labeled phosphate group, and detecting the incorporation, if any, of label into the mycoplasma RNA. In a further preferred embodiment, more than one phosphate group of the oligonucleotide is labeled and the RNA is ribosomal RNA.

Alternate labeling methods include radioactive, colorimetric and biochemical labels, with $^{32}$P being the most preferred label. Alternative labels include $^{35}$S-phosphorothioate. In an even more preferred embodiment, the step of detecting incorporation of the nucleotides comprises gel electrophoresis of the sample.

The sample can advantageously be a biological sample of mammalian cells, most preferably, mammalian cells are taken from a human. Alternatively, the mammalian cells are from the group consisting of HeLa cells, IMR-32 cells, and TC106 cells. In addition, the oligonucleotide of the preferred method can be either an oligoribonucleotide or oligodeoxyribonucleotide.

The method of the present invention can also advantageously include detecting mycoplasma selected from the group consisting of *Mycoplasma pneumoniae*, *Mycoplasma fermentans*, *Mycoplasma hominis* and *Mycoplasma arginini*.

A separate embodiment of the present invention includes a method for identifying a mycoplasma species in a sample, including the steps of:
  incubating the sample with oligonucleotides having a labeled phosphate group;
  isolating RNA from the sample, wherein mycoplasma RNA has been labeled by incorporation of label from the oligonucleotides;
  contacting the RNA with DNA complementary to a mycoplasma species specific gene; and
  measuring the binding of the RNA to the complementary DNA, wherein detectable binding of labeled RNA identifies a mycoplasma species.

In a preferred embodiment of this method, the label is radioactive, most preferably $^{32}$P. Alternative labels can be colorimetric or biochemical.

The contacting step of the present invention can advantageously comprise a Southern Blot. In addition, the sample taken to identify a mycoplasma species can be a biological sample from a mammal, preferably a human.

DETAILED DESCRIPTION

The present invention relates to the discovery that mycoplasma readily take up and process phosphorous labeled oligonucleotides. Phosphorous labeled oligonucleotides are defined as those oligonucleotides containing a label attached to one or more of the phosphorous atoms of any nucleotide in the sequence. This label can be radioactive, colorimetric, biochemical, or of any other design permitting one of skill in the art to detect incorporation of the label into mycoplasma RNA.

Without limiting the invention to any particular theory of operation, we believe the oligonucleotides of the present invention are digested into mononucleotides, with the label (such as $^{32}P$) being subsequently incorporated into endogenous mycoplasma RNA. Thus, one aspect of the invention comprises use of labeled oligonucleotides in general for detecting mycoplasma contamination. This is in contrast to prior art use of low-level radioactive (eg: $^{3}H$ labeled) mononucleotides in mycoplasma detection.

The present method of using phosphorous labeled oligonucleotides is far superior to past procedures which relied upon mycoplasma uptake of tritiated mononucleotides. The preferred embodiment of the present invention utilizes $^{32}P$, a substantially more powerful radioactive isotope than $^{3}H$. Prior to the present invention method, however, there was no successful procedure for preferentially incorporating $^{32}P$ into mycoplasma RNA.

Although radioactive phosphorous isotopes ($^{32}P$) represent a preferred embodiment, other labels (such as $^{35}S$ phosphorothioate) may be used, as described in the examples below to detect mycoplasma contamination of cell cultures.

The mechanism by which mycoplasma rapidly uptake and incorporate phosphorous labeled oligonucleotides, but not mononucleotides, is still under investigation. However, this discovery makes possible the rapid mycoplasma detection procedure of the present invention. The present invention procedure may be used in connection with cell cultures or alternatively with biological samples from living organisms.

The preferred detection procedure relies on the difference between the ribosomal RNA sizes of mammalian cells (eukaryotes) and mycoplasma (prokaryotes). Mycoplasma ribosomal RNA electrophoretically migrates on a gel at the 5S (approximately 107 bp), 16S (approximately 1.52 kb), and 23S (approximately 3.0 kb) positions, differing from the mammalian 18S and 28S ribosomal RNAs. Thus, incorporation of label from a sample into RNA sizes corresponding to mycoplasma ribosomal RNAs indicates a contamination.

including biological samples from living organisms (e.g., vertebrates, mammals, domestic animals, and humans).

The first step of the procedure is synthesizing and phosphorous-labeling an oligonucleotide sequence. This sequence is then incubated with the potentially contaminated sample to allow uptake and incorporation of label by the mycoplasma.

EXAMPLE 1

Synthesis and $^{32}P$ Labeling of Oligonucleotides oligonucleotides were synthesized with a commercial synthesizer (Model 380B; Applied Biosystems, Foster City, Calif.) and commercial reagents using the phosphoramidite methodology. The oligonucleotides were purified by ethanol precipitation. An oligonucleotide with a 3'-amine linker was prepared using a 3'-Amino-Modifier synthesis column (Glen Research, Sterling, Va).

Oligodeoxynucleotides were 5' end-labeled by reaction with $[\gamma-^{32}P]ATP$ and T4 polynucleotide kinase, followed by purification using a NENSORB-20 © column. This procedure resulted in oligonucleotides with SEQ ID NOS: 1-2.

Oligonucleotides with 3'-end-labels were created by reaction with $[\alpha-^{32}P]dATP$, catalyzed by terminal deoxynucleotide transferase. The 3' tailing reaction was followed by purification as above, resulting in SEQ ID NO: 3.

To make the internally labeled 18 base long oligodeoxynucleotide SEQ ID NO: 4, a 9-mer with a sequence corresponding to the 3' half of the final oligonucleotide was 5' end-labeled as explained above and ligated to a 9-mer containing the 5' half of the final sequence. A 21-mer template with sequence homology to the ligated product was used to align the sequences. The resultant 18-mer was purified from the template and shorter strands using denaturing polyacrylamide gel electrophoresis (PAGE). Following PAGE the 18-mer was isolated by excising and extracting the proper gel band.

A version of the oligonucleotide labeled with a $[^{3}H]$guanine in the 3'-position (SEQ ID NO: 5) was prepared by reaction with $[8-^{3}H]dGTP$ (NEN Dupont, Boston, Mass.) catalyzed by terminal deoxynucleotide transferase and subsequent purification by a NENSORB © column and ethanol precipitation.

The following is a list of each oligonucleotide sequence and its corresponding sequence ID number:

| | |
|---|---|
| ($^{32}P$) GATCA TGCCC GGCAT | (SEQ ID NO: 1) |
| ($^{32}P$) GATCA TGCCC GGCATp-CH$_2$CHOHCH$_2$NH$_2$ | (SEQ ID NO: 2) |
| GATCA TGCCC GGCAT ($^{32}P$)A | (SEQ ID NO: 3) |
| GCTGA TCAT ($^{32}P$)G CCCGG CAT | (SEQ ID NO: 4) |
| GATCA TGCCC GGCATp ($^{3}H$—G)] | (SEQ ID NO: 5) |

The rapid uptake of oligonucleotides by mycoplasma raises important caveats for studies using antisense technology. It is quite possible that mycoplasma contamination in antisense RNA or DNA experiments would skew the results by metabolizing nucleotides that would otherwise be free to enter the mammalian cells.

The following examples outline procedures for testing mammalian cell cultures for mycoplasma contamination by one embodiment of the inventive method. The general procedures described in these examples may also be used for determining mycoplasma contamination of samples from sources other than cell culture, The oligonucleotides listed as SEQ ID NOS: -5 are the preferred embodiment sequences. However, any phosphorous labeled oligonucleotide which is preferentially absorbed by mycoplasma is within the scope of the present invention.

For instance, $^{35}S$-phosphorothioate labeled oligonucleotides can be produced in a manner similar to that outlined in Example 1. To prepare a 5' end-label, the oligodeoxynucleotide is, for instance, reacted with $\gamma-[^{35}S]$-ATP catalyzed with T4 kinase by methods known in the art. To prepare a 3' end-label, the oligonucleotide is, for example, reacted with α−[35S]-dATp catalyzed by terminal deoxynucleotide transferase, also by methods known in the art.

Example 2 below details the preferred method of preparing mycoplasma samples and infected cell lines. Other methods of preparing these samples and cell lines are also within the purview of the present invention.

EXAMPLE 2

Preparation of Mycoplasma and Infected Cell Lines

Mycoplasma cultures

Mycoplasma cultures were grown in modified Edward's medium (Chandler et al. (1982) Infect. Immun. 38: 604–609). Cultures of four mycoplasma species; *Mycoplasma pneumoniae* (strain M129), *Mycoplasma fermentans* (strain PG18), *Mycoplasma hominis* (strain 1620) and *Mycoplasma arginini* (strain G230), were chosen.

Infected Cell Lines

A culture of HeLa cells (human cervical carcinoma) grown in Dulbecco's modified Eagle's medium (DMEM) and 10% fetal bovine serum (FBS) with penicillin and streptomycin was found to be infected with *M. arginini* (species typing by Frederick cancer Research Facility, Frederick, Md.). Mycoplasma contamination of the HeLa cell culture was confirmed by a detection kit based on adenosine phosphorylase activity with 6-methylpurine deoxyriboside as substrate (Mycotect; GIBCO/BRL, Bethesda, Md.).

EXAMPLE 3

Labeling of Mycoplasma Cultures

Aliquots of the radioactively labeled oligonucleotides from Example 1 were dissolved in phosphate-buffered saline (PBS). Approximately 10 μCi was added to mycoplasma cultures growing in T-25 flasks containing 10 mls growth medium. The cultures were then incubated for 2 h at 37° C., followed by scraping the flask walls and centrifuging the mycoplasma pellet. The supernatant was removed, and the pellet was treated with RNAZOL B © (Tel-Test, Friendswood, Tex.). RNA was then harvested using the standard RNAZOL B © method. Total RNA concentration was determined by absorbance at 260 nm, and total RNA radioactivity was determined by scintillation counting. Samples of the RNA were electrophoresed on a 1.2% agarose, formaldehyde and 3-(N-morpholino) propanesulfonic acid (MOPS) gel at 200 V. The gel was dried and placed in an autoradiography folder.

RNA molecular size markers were also run on the gel, followed by ethidium bromide staining and UV fluorescence. In samples containing the tritiated oligonucleotides, the gel lane was cut into pieces and analyzed by scintillation counting.

Results

When each of the four species of mycoplasma were treated with 5'-end-labeled oligonucleotide SEQ ID NO: 1 and subsequently RNA harvested and electrophoresed, the ethidium fluorescence showed the expected bands for the 23S (approximately 3.0 kb), 16S (approximately 1.52 kb) and 5S (approximately 107 b) rRNAs. The band positions were essentially identical for each of the four species.

The autoradiograph, however, showed several distinct bands in each lane (FIG. 1). In each case, the 23S and 16S rRNAs appear to be labeled, but other RNA species are labeled as well, leading to a distinct pattern in each of the four species.

*M. pneumoniae* (lane 1) shows radioactivity in bands at 3.3 kb (just above the 23S) and at 1.85 kb (just above the 16S band), as well as bands at 390 and 240 bases. In *M. arginini* (Lanes 2 and 5), a distinct band appears at 4.0 kb and there is a multiplet of bands in the 16S region from 2.0 to 1.4 kb, as well as bands at 950 and 440 bases; the 5S band is also visible. *M. fermentans* (lanes 3 and 6) shows a band at 1.75 kb and a band at about 410 bases; the 5S band is also strongly radioactive. *M. hominis* (lane 4), however, shows only the 16S and 23S bands.

The efficiency of labeling, based on cpm/μg RNA harvested, varied greatly among the species, despite the approximately equal cell numbers and RNA yield. Thus, RNA from *M. fermantans* was labeled approximately 20 times greater than *M. arginini*, which in turn was labeled about 10 times greater than *M. pneumoniae* or *M. hominis*. These results show that 5' end-labeled oligonucleotides can efficiently label many different mycoplasma species. However, the efficiency of labeling may be different for each species.

Figure 2:
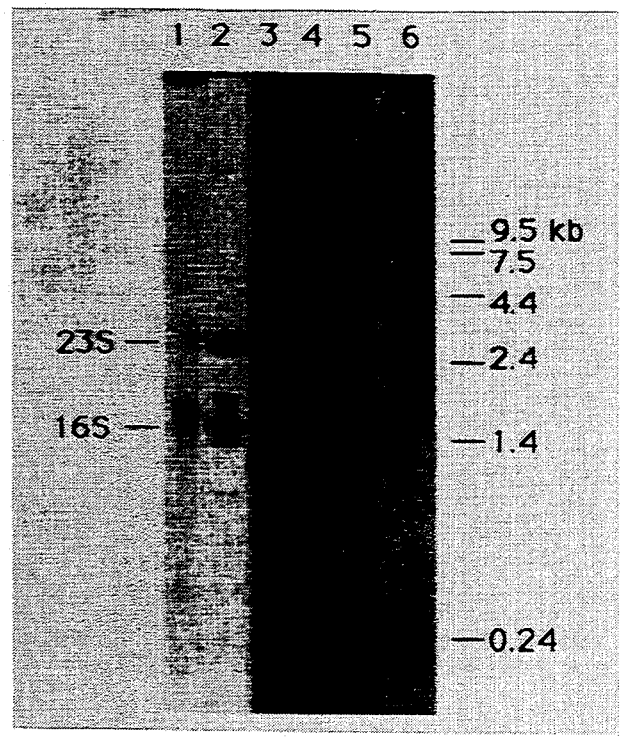
FIG. 2. Incorporation of radiophosphorus from end-labeled oligonucleotide 1 (SEQ ID NO: 1), 3'-labeled oligonucleotide 3 (SEQ ID NO: 3), and internally labeled oligonucleotide 4 (SEQ ID NO: 4) into RNA of *M. pneumoniae* and *M. arginini*. Cultures were incubated for 2 h before harvesting and electrophoresis as in FIG. 1. Lanes 1, 3, and 5, *M. pneumoniae*; lanes 2, 4, and 6, *M. arginini*. Lanes 1 and 2, oligonucleotide 1 (SEQ ID NO: 1); lanes 3 and 4, oligonucleotide 3 (SEQ ID NO: 3); lanes 5 and 6, oligonucleotide 4 (SEQ ID NO: 4). Lane exposures do not reflect relative efficiencies of labeling with the different oligonucleotides.

The patterns observed when the 3'-labeled oligonucleotide (SEQ ID NO: 3) and the internally labeled oligonucleotide SEQ ID NO: 4 were incubated with *M. arginini* and *M. pneumoniae* were essentially the same as those seen with SEQ ID NO: 1 (FIG. 2). Scintillation counting of the electrophoresed RNA from the tritium-labeled oligonucleotide SEQ ID NO: 5 also indicated radioactivity in the vicinity of the 28S and 16S rRNA bands, although detailed resolution of the band pattern was not possible.

Based on the ratio of radioactivity present in total RNA harvested to the amount added to each culture, the efficiency of oligonucleotide utilization by *M. arginini* and *M. pneumoniae* was within an order of magnitude for oligos SEQ ID NOS: 1, 3, 4 and 5.

Thus, efficient uptake of phosphorous-labeled oligonucleotides into mycoplasma RNA is possible from label in any number of positions on the oligonucleotide. The pattern of RNA incorporation was unaffected by the position of the label in the nucleotide sequence.

Although the successful uptake of phosphorous-labeled oligonucleotides had now been demonstrated, it was still necessary to show that mycoplasma absorbed these sequences at a much higher rate than other cell types. Example 4 was performed to demonstrate the preferred uptake of phosphorous labeled oligonucleotides by mycoplasma in an infected HeLa cell line.

EXAMPLE 4

Labeling of Infected Cell Lines

An aliquot of each labeled oligonucleotide, approximately 10 μCi, was added to a flask containing HeLa cells adventitiously infected with *M. arginini* by the method of Experiment 2. The flask was incubated at 37° C. for 2 h in a 5% CO2 atmosphere. The supernatant was subsequently removed and the adherent cells were treated with RNAZOL B © followed by an RNA isolation and gel electrophoresis as described in Example 3.

When the HeLa cell line was treated with end-labeled oligonucleotide SEQ ID NO: 1, the total RNA obtained from the cell culture appeared by ethidium staining to contain only human RNA, as evidenced by prominent 28S and S RNA bands. Upon autoradiography, however, the 28S and S bands showed no radioactive 32P incorporation. A pattern of labeled bands was seen that was very similar to that found in pure cultures of *M. arginini* (FIG. 3)

Figure 3:
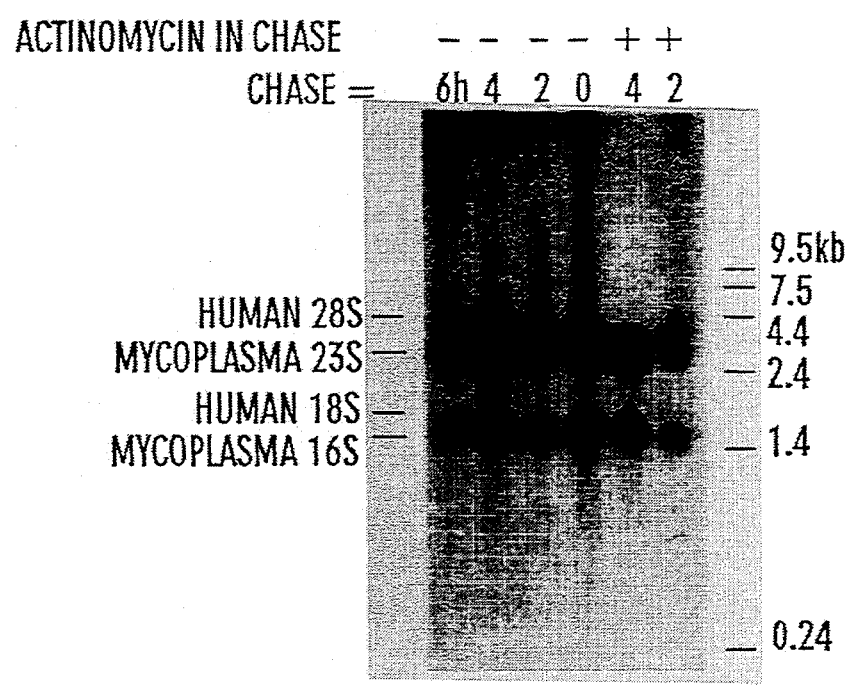
FIG. 3. Pulse chase of *M. arginini*-infected HeLa cells with end-labeled oligonucleotide 1 (SEQ ID NO: 1). Wells containing the infected cells were incubated for 2 h with oligonucleotide 1 (SEQ ID NO: 1) and were then washed with unlabeled medium. Wells were then harvested for RNA at 0, 2, 4, and 6 h (as labeled). The two rightmost lanes were wells of infected cells washed with unlabeled medium containing actinomycin D (4 μg/ml) at time 0. RNA was harvested from these wells 2 and 4 h after this chase. Following harvest, the RNA was electrophoresed and the gel autoradiographed.

Thus, although the mycoplasmal RNA represented only a small fraction of the total RNA isolated from the cell culture, only the mycoplasmal RNA was labeled, evidenced by the distinctive *M. arginini* autoradiographic pattern (FIG. 3).

As expected, when several mammalian cell lines that tested negative for mycoplasma infection (controls) were treated with radioactive oligonucleotides and their RNA harvested, no labeled RNA species were detectable. The HeLa cells were apparently unable to incorporate the phosphorous label from the exogenous oligonucleotide sequences into their RNA.

To demonstrate that the radiolabel was being incorporated during RNA synthesis, the infected HeLa cell line was treated with actinomycin D simultaneously with oligonucleotide SEQ ID NO: 1 incubation.

Actinomycin D completely disrupts RNA synthesis. If the label was transferred to the RNA after transcription, some of the RNA would become labeled after the incubation. However, if the label was incorporated before, or during transcription, no label would be added to the RNA sequences.

After actinomycin D treatment, incorporation of label into RNA was completely inhibited. The label is therefore incorporated before or during transcription.

Other labeled oligonucleotides, including a 3'-modified oligonucleotide SEQ ID NO: 2 and a scrambled version of SEQ ID NO. 2 in which the 5' base is a T, also led to rapid incorporation of radiophosphorus into *M. arginini* RNA. $^{32}$P was also found to be very efficiently incorporated from a radioactive RNA transcript. Labeled RNA transcripts thereby provide and additional method of detecting mycoplasma contamination. However, as expected, labeled mononucleotides (i.e.: [$\alpha-^{32}$P]dCTP) don't possess the rapid incorporation advantage seen with oligonucleotides and oligoribonucleotides.

The RNA transcript, in this experiment, was purchased pre-labeled with $^{32}$P. An additional method of producing labeled RNA is outlined in Example 5 below. When [$\gamma-^{32}$P]ATP or [$\gamma-^{32}$P]-orthophosphate was used, no incorporation of radiophosphorus was observed, as expected (Table 1).

TABLE 1

| Qualitative Efficiency of Incorporation of Radiolabel from Various Substrates into Mycoplasma RNAs | |
|---|---|
| Substrate | Relative RNA Incorporation Efficiency |
| [$^{32}$P]RNA | +++ |
| [4'-$^{32}$P]oligodeoxynucleotide | ++ |
| [5'-$^{32}$P]oligodeoxynucleotide with 3'-amine link | ++ |
| Internally $^{32}$P-labeled oligodeoxynucleotide | ++ |
| 3'-$^{32}$P-labeled oligodeoxynucleotide | ++ |
| [3'-$^{32}$P]A labeled oligodeoxynucleotide | +++ |
| [3'-$^{32}$P]G labeled oligodeoxynucleotide | +++ |
| [3'-$^{32}$P]C labeled oligodeoxynucleotide | +++ |
| [3'-$^{32}$P]T labeled oligodeoxynucleotide | +++ |
| [5'-$^{32}$P]A labeled oligodeoxynucleotide | +++ |
| [5'-$^{32}$P]G labeled oligodeoxynucleotide | +++ |
| [5'-$^{32}$P]C labeled oligodeoxynucleotide | +++ |
| [5'-$^{32}$P]T labeled oligodeoxynucleotide | +++ |
| 3'-$^3$H-G-labeled oligodeoxynucleotide | ++ |
| [$\alpha$-$^{32}$P]dCTP | + |
| [$^{32}$P]orthophosphate | − |
| [$\gamma$-$^{32}$P]ATP | − | a The symbols are an estimate of relative incorporation efficiency based on visual analysis of autoradiographs: +++, relatively high; ++, moderate; +, relatively little; −, no observed incorporation.

Other embodiments of the present identification method are contemplated using alternative cell lines such as IMR-32 (human neuroblastoma) and TC106 (Ewing's sarcoma) in place of the preferred HeLa cell line.

Table 1 also reflects that the particular base that is chosen to be labeled, and the position of that base within the oligonucleotide (i.e.: 5', 3', or central) makes no difference on the efficiency of label incorporated into the mycoplasma RNA.

Although oligodeoxynucleotides were used for the preferred labeling method, oligoribonucleotides are also efficiently taken up and incorporated by mycoplasma. Example 5 describes one method of preparing phosphorous labeled oligoribonucleotides.

EXAMPLE 5

Labeling of Oligoribonucleotides

Oligoribonucleotide sequences are synthesized by cleavage and transcription of a LIBRARIAN II© (Invitrogen Corp, San Diego, Calif.) *E. Coli* expression plasmid. The LIBRARIAN II© plasmid is linearized with EcoRI by methods known to those of skill in the art, and transcribed in the presence of $^{32}$PdATP by the INVITROSCRIPT© transcription kit (Invitrogen, San Diego, Calif.).

Briefly, INVITROSCRIPT© is an in vitro transcription system which relies on the Sp6 phage promoter to synthesize high specific activity RNA sequences from Sp6-containing plasmids, such as the LIBRARIAN II.

In addition to the previous experiments, we were interested in determining the method of oligonucleotide incorporation into mycoplasma RNA. Pulse-chase experiments were performed, as outlined in Example 6, to analyze the pathway and mechanism of label incorporation into the mycoplasma RNA.

EXAMPLE 6

Pulse-Chase Experiment

The infected HeLa cell culture was grown in a six-well microtiter plate. Each well was treated with 5 $\mu$Ci of end-labeled oligonucleotide for 2 h and then washed with fresh medium and incubated for 0, 2, 4 or 6 h before RNA extraction. Two additional wells were treated with actinomycin D (4 $\mu$g/ml) after washing (to inhibit RNA synthesis) and the RNA extracted after 2 or 4 h. The RNA samples were electrophoresed on a 1.2% agarose gel, which was then dried and autoradiographed.

When the infected HeLa cell line was pulsed with radioactive oligonucleotide SEQ ID NO: 1 for 2 h followed by a chase period of 0–6 h, the total RNA obtained again showed evidence of radioactivity only in the mycoplasmal sequences, with the human RNA remaining unlabeled (see FIG. 3). The distinctive pattern of *M. arginini* was seen in the autoradiograph at 0 h. Over the chase period, the intensities of the 23S and 16S ribosomal RNA bands remained fairly constant, but several of the other bands faded relative to the rRNAs, most notably the band at 4.0 kb. The multiplet just above the 16S rRNA also weakened, although this is not as visible in FIG. 3.

Thus, many of the bands, other than the major rRNAs, are probably short-lived species. It is not known if these represent mRNAs or rRNA precursors. Addition of actinomycin D during the chase period for 2–4 h (FIG. 3 far right lanes) makes little difference in the bands observed, consistent with effective removal of the label in the cold chase step.

An additional embodiment of the present method, includes using the rapidly labeled mycoplasma RNA for determining the type of mycoplasma species in a sample. The sample could be from a cell culture, or a biological sample (i.e.: blood, urine, mucus etc). Example 7 describes a method of determining the type of mycoplasma species in a sample.

EXAMPLE 7

Mycoplasma Species Determination

A flask containing a HeLa cell sample is found to be infected by an unknown mycoplasma species as outlined in Experiment 2. The sample is incubated with oligonucleotide SEQ ID NO: 1 as described in Experiment 4. RNA is isolated from the sample, by the methods described above, and used to probe a Southern Blot by methods known to those in the art. The Southern Blot contains individual lanes of DNA samples bound to a nitrocellulose membrane. The DNA in each lane is specific to a particular mycoplasma species.

The species specific DNA samples are isolated by the methods of Gobel et al. (*Journal of General Microbiology* (1987) 133: 1969–1974). Briefly, total genomic DNA from each mycoplasma is isolated, restriction enzyme digested and cloned into plasmid pUC8 by well known methods. Plasmids carrying fragments of the 16S ribosomal RNA gene are identified by a labeled probe containing *E. Coli* 16S rRNA sequences (Brosius et al. *Proc. Nat. Acad. Sci.* (1978) 75: 4801–4805). Those mycoplasma sequences with homology to 16S rRNA are nucleotide sequenced by Sanger dideoxy chain termination. The regions of the rRNA having large nucleotide sequence variations between species are identified and chosen as oligonucleotide templates. Oligonucleotides corresponding to 16S rRNA variable regions are synthesized by an Applied Biosystems 380A DNA synthesizer. Each oligonucleotide, corresponding to a sequence specific for a particular mycoplasma species 16S rRNA, is then run on an acrylamide gel and blotted to nitrocellulose.

The labeled mycoplasma RNA binds to the lane containing *M. arginini* specific DNA, and no other lane. The unknown mycoplasma is thereby determined to be *M. arginini*.

Other methods, differing from a Southern Blot (i.e.: Northern Blot, RNA runoff, Dot Blot etc.) which use the labeled mycoplasma RNA to determine species typing are within the scope of the present invention.

One further embodiment of the present invention includes the method of determining mycoplasma contamination of a biological sample. This sample could be, for instance, blood, urine, mucus, or cells derived from the organism being tested. Preferably the organism is a mammal, and most preferably, a human.

Example 8 reveals one method for determining mycoplasma infection in a human.

EXAMPLE 8

Detection of Mycoplasma Infection in a Biological Sample

A sample of blood is drawn from a person suspected of being infected with mycoplasma. The sample is incubated with $^{32}P$ labeled SEQ ID NO: 1 as described above. RNA is then isolated from the blood sample and run on an agarose gel by methods known in the art.

Ethidium bromide staining of the gel shows many RNA species, however, autoradiography of the dried gel reveals bands at only the 23S and 16S positions. These bands indicate a mycoplasma infection, since mammalian rRNA bands migrate to different positions.

To confirm that the contamination is by mycoplasma, and not some other prokaryotic species, the labeled RNA is used to probe a Southern Blot containing mycoplasma-specific DNA. Hybridization to the *M. arginini* lane on the blot confirms the presence of a mycoplasma (*M. arginini*) infection.

Although this experiment is performed with $^{32}P$ labeled oligonucleotides, other methods are available for labeling and detecting positive hybridization. These methods include colorimetric and biochemical assays involving biotinylated DNA. Although the biotin-streptavidin system is the one way of carrying out these experiments, it is not the only method. Other methods of non-radioactively labeling and detecting DNA probes are also contemplated by the present invention.

Example 9 details two methods of non-radioactively labeling oligonucleotides and further detecting the incorporation of that label into mycoplasma RNA.

EXAMPLE 9

Non-Radioactively Detecting Oligonucleotide Label Incorporation

Biochemical labels using systems such as avidin-biotin can be used with the present invention to detect incorporation of label by, for instance, chemiluminescence. The following protocol reveals one method of biotin labeling a DNA sequence, and detecting the incorporation of that label into mycoplasma RNA.

An oligonucleotide is nick-translated with the BIONICK © system (GIBCO-BRL) in the presence of dCTP, dGTP, dTTP and a biotinylated dATP analog. The biotin molecule is attached to one of the dATP's phosphate groups, therefore becoming incorporated into the oligonucleotide. A HeLa cell culture infected with *M. arginini* is incubated with the biotinylated oligonucleotide. RNA is isolated from the culture, and used to probe a Southern blot containing mycoplasma specific DNA by methods well known in the art. Hybridization of the biotin-labeled oligonucleotide to the *M. arginini* DNA is visualized using the PHOTOGENE © system (GIBCO-BRL) comprising a streptavidin-alkaline phosphatase conjugate. The PHOTOGENE © system chemiluminescently indicates a positive hybridization. This method confirms both the mycoplasma contamination and species type.

One additional method of detecting biotin labeled mycoplasma RNA is through colorimetric change. The above biotinylated oligonucleotide can be used in a similar procedure for detecting a M. arginini contamination by using the BLUGENE © system (GIBCO-BRL) to provide a colorimetric indication of a positive hybridization, instead of the chemiluminescent method already disclosed. Although these are some methods of detecting label incorporation into mycoplasma RNA, any method known to those with skill in the art is within the scope of this invention.

DISCUSSION

We have demonstrated that mycoplasmas have the ability to rapidly incorporate labeled phosphorous from any position in an exogenously added oligonucleotide into their newly synthesized RNA. The incorporation of the labeled phosphorus from γ-ATP or orthophosphate was not detectable in our system. A qualitative summary of the relative efficiency of incorporation from various substrates is given in Table 1. These results are consistent with a process in which the mycoplasmas take up the oligonucleotide, digest and remove the phosphorous label, and link it to new ribonucleotides, which are then used in RNA synthesis.

The similarity of efficiencies with 5'-, internally, and 3'-labeled oligonucleotides suggests complete digestion of the sequence prior to RNA incorporation. However, the mechanism of DNA to RNA conversion was not revealed by these experiments. The lack of observed incorporation from γ-ATP suggests that the mycoplasma prefer to incorporate intact 5'-nucleotides rather than use ATP as a phosphate source in nucleotide synthesis.

We have seen incorporation when the radiophosphorus is 5' to T, A, G or C (Table 1). The presence of an amine linker on the 3' end of the oligonucleotide made no difference; apparently this modification has little effect on the enzymes thought responsible for oligonucleotide digestion. The preceding results suggest that the mycoplasma are very efficient at digesting a variety of oligonucleotides.

Presumably, mycoplasmas can efficiently accumulate a variety of nucleosides, nucleotides or oligonucleotides from the surrounding medium. Thus, mycoplasma infection would almost certainly interfere with the results of any study requiring the uptake and utilization of these molecules by mammalian cells.

Plainly, mycoplasma must generally be avoided in antisense experiments in vitro. If the potential for antisense therapeutics is ever to be realized, however, the occurrence of mycoplasmas in the patient must be considered. Mycoplasma colonization is ubiquitous in people. *M. fermantans* has received particular attention recently as an important pathogen in patients with the acquired immunodeficiency syndrome (AIDS) (Bauer, et al. (1991) *Hum. Pathol.* 22: 63–69).

Although these results raise caveats with respect to antisense research, our findings have useful consequences for mycoplasma contamination and infection. First, the present invention method of RNA labeling may be used as a rapid and sensitive method for detection of mycoplasma contamination in cell cultures and biological samples. The lack of host cell labeling limits the background signal even when the mycoplasma level is extremely low. Indeed, in one case we were easily able to detect the presence of mycoplasmal RNA in a culture of TC106 cells, but a positive response using the MYCOTECT © detection kit required 5 days.

The present invention therefore provides an advantageous method of determining mycoplasma contamination, even in cell populations where detection was previously difficult and slow to obtain.

---

We claim:

1. A method for detecting mycoplasma in a sample, comprising the steps of:
   incubating said sample with oligonucleotides having a $^{32}P$ labeled phosphate group, and
   detecting the incorporation, if any, of label into the mycoplasma RNA.

2. The method of claim 1 wherein more than one phosphate group of said oligonucleotide is labeled.

3. The method of claim 1 wherein said detection step comprises gel electrophoresis of said sample.

4. The method of claim 1 wherein said mycoplasma RNA is ribosomal RNA.

5. The method of claim 1 wherein said sample is a biological sample of mammalian cells.

6. The method of claim 5 wherein said mammalian cells are taken from a human.

7. The method of claim 5 wherein said mammalian cells are selected from the group consisting of HeLa cells, IMR-32 cells, and TC106 cells.

8. The method of claim 1 wherein said oligonucleotide is either an oligoribonucleotide or oligodeoxyribonucleotide.

9. The method of claim 1 wherein said mycoplasma is selected from the group consisting of *Mycoplasma pneumoniae, Mycoplasma fermentans, Mycoplasma hominis* and *Mycoplasma arginini.*

10. A method for identifying a mycoplasma species in a sample, comprising the steps of:
    incubating said sample with oligonucleotides having a $^{32}P$ labeled phosphate group;
    isolating RNA from said sample, wherein mycoplasma RNA has been labeled by incorporation of $^{32}P$ from said oligonucleotides;
    contacting said RNA with DNA complementary to a mycoplasma species specific gene; and
    measuring the binding of said RNA to said complementary DNA, wherein detectable binding of labeled RNA identifies a mycoplasma species.

11. The method of claim 10 wherein said contacting step comprises a Southern Blot.

12. The method of claim 10 wherein said sample is a biological sample from a mammal.

13. The method of claim 12 wherein said mammal is a human.

* * * * *